United States Patent [19]

Warner et al.

[11] 4,455,392

[45] Jun. 19, 1984

[54] PROCESS FOR PREPARING A SUPPORTED SILVER CATALYST

[75] Inventors: Glenn H. Warner, St. Albans; Madan M. Bhasin, Charleston, both of W. Va.; Bernard Lieberman, Kew Gardens, N.Y.

[73] Assignee: Union Carbide Corporation, Danbury, Conn.

[21] Appl. No.: 308,653

[22] Filed: Oct. 5, 1981

[51] Int. Cl.$^3$ .................. B01J 23/04; B01J 23/50
[52] U.S. Cl. ...................... 502/347; 549/534
[58] Field of Search .............. 252/476; 260/348.34; 502/347; 549/534

[56] References Cited

U.S. PATENT DOCUMENTS

| | | | |
|---|---|---|---|
| 3,563,914 | 2/1971 | Wattimena | 252/463 |
| 3,725,307 | 4/1973 | Brown et al. | 252/455 R |
| 3,962,136 | 6/1976 | Nielsen et al. | 252/454 |
| 4,010,115 | 3/1977 | Nielsen et al. | 252/454 |
| 4,012,425 | 3/1977 | Nielsen et al. | 260/348.5 R |
| 4,033,903 | 7/1977 | Maxwell | 252/476 |
| 4,066,575 | 1/1978 | Winnick | 252/475 |
| 4,168,247 | 9/1979 | Hayden et al. | 252/476 |
| 4,207,210 | 6/1980 | Kilty | 252/463 |
| 4,248,740 | 2/1981 | Mitsuhata et al. | 252/463 |
| 4,267,073 | 5/1981 | Nielsen et al. | 252/455 R |
| 4,278,562 | 7/1981 | Mross et al. | 252/412 X |

FOREIGN PATENT DOCUMENTS

| | | |
|---|---|---|
| 793658 | 7/1973 | Belgium. |
| 2914640 | 10/1980 | Fed. Rep. of Germany. |
| 54-79193 | 6/1979 | Japan. |
| 1489335 | 10/1977 | United Kingdom. |
| 2045636 | 11/1980 | United Kingdom. |

*Primary Examiner*—W. J. Shine
*Attorney, Agent, or Firm*—Norman L. Balmer

[57] ABSTRACT

This invention relates to a supported silver catalyst for the manufacture of ethylene oxide prepared by a process comprising impregnating a porous catalyst support with a solvent containing a silver salt and treating the impregnated support to effect deposition of silver on the support surface. Following silver deposition, the support is impregnated with a liquid containing more than 30%, by volume, of an organic solvent capable of forming a complex with silver ion, and a compound of at least one metal promoter in an amount sufficient to deposit the desired amount of metal cation on said support. The impregnated support is then treated to effect deposition of the promoter. There is also described herein a process of making such catalyst and a process for producing ethylene oxide.

9 Claims, No Drawings

PROCESS FOR PREPARING A SUPPORTED SILVER CATALYST

This invention relates to supported silver catalysts for the manufacture of ethylene oxide, their preparation, and their use in ethylene oxide processes. More specifically, the invention is concerned with preparing a metal cation promoted silver catalyst capable of oxidizing ethylene with an oxygen-containing gas in the vapor phase to produce ethylene oxide at high efficiencies.

In characterizing catalysts useful for the manufacture of ethylene oxide, the term "selectivity" is employed herein as defined in U.S. Pat. No. 3,420,784, patented Jan. 7, 1969, at column 3. The terms "efficiency" and "selectivity" as used throughout the specification with regard to the aforesaid catalysts are intended to be synonymous.

Processes for preparing metal cation-promoted silver catalysts for the production of ethylene oxide are extensively described in the patent literature. The vast majority of these processes employ impregnation techniques wherein solutions containing solubilized compounds of silver and metal cation promoters are used to impregnate a porous carrier or support followed by heat treatment of the impregnated support to effect deposition of the silver and metal cation on the support. Processes for making coated catalysts employ techniques wherein silver and metal cations are coated onto a catalyst support from an emulsion or slurry followed by a heating step to remove the liquid present from the carrier and effect deposition of the silver and metal promoter. Coated catalysts are generally considered today to be less satisfactory than impregnated catalysts in commercial practice because it is generally believed that coating methods are unable to accomplish substantial deposition of silver into the interior surfaces of the carrier and consequently, the coated catalysts are more susceptible to silver loss by mechanical abrasion.

The impregnation methods described in the art for preparing ethylene oxide catalysts include a wide variety of methods of depositing silver and metal cations onto a carrier. These methods are generally distinguished by the process conditions they employ such as low-temperature impregnation, high temperature impregnation, activation in an inert gas atmosphere and/or choice of solvent for the silver impregnating solution.

Criticality is often taught to reside in the order of addition of the metal cation and silver to the carrier. Such processes are characterized by their employing either a coincidental (or simultaneous) method of depositing silver and metal cation onto the carrier or a sequential method of addition wherein silver is added either before or after the metal cation. The addition of silver to a carrier subsequent to the addition of metal cation is referred to herein as a "metal-first" sequential process of preparation, while the addition of silver to the carrier prior to the addition of the metal cation is referred to herein as a "silver-first" method of preparation. The coincidental (or simultaneous) addition of silver and metal cation to a carrier is referred to herein as a "coincidental method" of preparation. The use of the term "addition" of a metal cation and/or silver to a carrier is meant to include the steps of impregnating the porous carrier with a solution containing silver and/or metal cation, as the case may be, followed by deposition of same upon the carrier, usually by heat treatment.

The comparative performance of catalysts produced by coincidental and sequential methods of impregnation has been reported in the art. For example, U.S. Pat. No. 3,563,914 to Wattimena, in Table III, compares the effect of the order of addition of alkali metal promoter and silver to a catalyst support on catalyst efficiency. The data in Table III is said to illustrate the advantage of adding an alkali metal promoter to the support before the silver compound. Specifically, the catalysts prepared by an alkali metal-first preparation procedure are shown to have an efficiency of 4-5 percent higher than catalysts prepared by a coincidental deposition of alkali metal and silver. Further, a catalyst prepared by the addition of silver to the carrier prior to alkali metal addition was by far the least efficient in that the selectivity was about 12 percent below that of a similar catalyst prepared by a coincidental method of deposition. In contrast with Wattimena's conclusion regarding the superiority of an alkali metal-first sequential order of addition, Belgian Pat. No. 793,658 and U.S. Pat. Nos. 3,962,136, 4,101,115 and 4,012,425 to Nielsen et al indicate that the coincidental deposition of silver and alkali metal is the preferred method of catalyst preparation insofar as it results in the highest catalyst efficiencies. The aforementioned Belgian patent also provides a direct comparison of catalysts prepared by a method of coincidental deposition of silver and potassium with catalysts of similar composition prepared by a sequential process wherein silver is deposited prior to potassium. Specifically, Example III of the Belgian patent indicates that the maximum efficiency achieved with catalysts containing 7.8 weight percent silver and varying amounts of co-deposited potassium was 76.3% under the stated test conditions whereas in Example VII of the patent the maximum selectivity achieved under the same conditions with catalysts containing the same amount of silver and similar amounts of potassium but prepared by a silver-first process was 73-74%, thus confirming the data in Wattimena concerning the inherent inefficiency of catalysts prepared by a silver-first sequential order of addition.

U.S. Pat. No. 4,207,210 to Kilty, based upon British specification No. 1 489 335, describes an alkali metal-first process for preparing ethylene oxide catalysts which is said to provide catalysts equivalent or even superior to those produced by coincidental methods of deposition such as set forth in the aforementioned U.S. patents to Nielsen et al. According to the described procedure of Kilty, an aqueous solution containing alkali metal is used to impregnate the porous carrier which is then dried to fix the alkali metal and thereafter the silver is supplied to the support. Tables A through E of the Kilty U.S. patent provide comparisons of catalysts prepared in accordance with the disclosed alkali metal-first method of addition with catalysts of similar composition prepared by the simultaneous addition of alkali metal and silver. The criticality of the alkali metal-first method of addition is, however, called into question by the reported data which fails to indicate any discernible difference between either method of preparation based on the measured catalyst efficiencies. Indeed, the alkali metal-first method of addition appears to be inherently identical to the coincidental deposition method used in the Nielsen et al patents as evidenced by the fact that both Kilty and Nielsen et al disclose that the alkali metal which is added to the carrier can be subsequently removed, if desired, using an alkanol solvent. This suggests that in the preparation procedure of Kilty, the alkali metal which is initially deposited on the carrier is resolubilized in the silver-containing impregnating solution thereby inherently effecting a coincidental deposition of silver and alkali metal. (Compare this to Wattimena, U.S. Pat. No. 3,563,914, discussed above.) This is further evidenced by a comparison of the curve shown in Kilty's British Patent Specification No. 1 489 335 wherein selectivity is plotted as a function of cesium content for a carrier having a surface area of 0.19 $m^2/g$, and the curve shown in Ser. No. 216,188, filed Jan. 7, 1972, now abandoned (the application from which the Nielsen et al U.S. patents were derived), wherein curve C represents as a function of cesium content the selectivities achieved with catalysts having an essentially similar silver content and alumina carrier to that used in the examples of Kilty but prepared by a coincidental method of deposition. The similarity of the two curves confirms the fact that the efficiencies produced with catalysts prepared by the coincidental method of Nielsen et al and the sequential method of Kilty are essentially equivalent.

As noted in the prior art, processes for preparing catalysts by the silver-first method have obvious drawbacks with regard to the resulting catalyst efficiencies. The prior art has documented the markedly lower efficiencies of catalysts produced by the silver-first method relative to similar catalysts prepared by a coincidental method, the latter appearing to be essentially equivalent to an alkali metal-first order of addition. Thus, as discussed above, U.S. Pat. No. 3,563,914 to Wattimena and Belgian Pat. No. 793,658 contain comparative data clearly illustrating the relative inefficiency of catalysts produced by a silver-first sequential method of addition relative to a coincidental method of addition. While other patents in the art directed to silver-first methods of preparation do not provide sufficient data to allow such side-by-side comparisons to be made, nevertheless, the data which is provided appears to indicate that silver-first methods are the less preferred methods. U.S. Pat. No. 4,033,903 to Maxwell, for example, discloses a silver-first method of addition wherein used ethylene oxide catalysts are reactivated by the addition of an alkali metal promoter to the aged catalyst. The process of the patent is said to be equally effective for enhancing the efficiency of freshly prepared catalysts by employing a heat treatment step intermediate to the steps of silver addition and alkali metal addition to the carrier. The effectiveness of this method of preparation seems somewhat doubtful, however, in view of the data shown in Table III of the patent wherein catalysts R and T, catalysts prepared by a silver-first method are shown to be inferior to catalyst Q, a silver catalyst containing no alkali metal promoter. Accordingly, based upon the data in the aforementioned patents there appears to be an obvious need in the art for a silver-first sequential method of catalyst preparation capable of providing catalysts which are no less efficient than those produced by the coincidental or metal-first methods.

A common characteristic of the various silver-first methods of preparation described in the literature is their use of the same solvents for metal cation addition. That is, the methods disclosed in this literature suggest using water or a lower alcohol, such as, methanol or ethanol, as the solvent for effecting metal cation impregnation. Thus, for example, the aforementioned patent to Wattimena describes in Example III a silver-first addition wherein water is employed as the solvent for the alkali metal impregnation step. Belgian Pat. No. 793,658 which discloses a silver-first method of addition in Example VII thereof states that aqueous solutions of potassium were used as the impregnating medium for the promoter. U.S. Pat. No. 4,066,575 to Winnick describes a process of catalyst preparation characterized by an activation step wherein the carrier is heated in an inert gas atmosphere following its impregnation with a silver solution. An alkali metal promoter is thereafter deposited on the carrier employing as a solvent for the alkali metal, water or a lower alkanol such as, methanol, ethanol or propanol. Great Britain Patent Application No. 2,045,636A attempts to distinguish itself from the prior art processes by its low-temperature deposition technique whereby the carrier impregnated with a silver-containing solution is maintained at temperatures below 200° C. prior to the so-called post deposition of alkali metal. The suggested solvents for such post-deposition of alkali metal are water and ethanol. German Offenlegungsschrift No. 2,914,640 discloses a sequential order of impregnation wherein silver is initially applied to the carrier from a suspension and the carrier thereafter immediately dried. Alkali metal is then added to the carrier from a solution using water as the solvent. U.S. Pat. No. 4,248,740 to Mitsuhata et al describes a catalyst preparation procedure employing a silver-first order of addition. The patentees recommend impregnating the carrier with an alkali metal solution containing water or a lower alcohol, such as methanol, ethanol or propanol. The solvent is then evaporated, care being taken to prevent heating of the catalyst to above 200° C., a critical feature of the described process. In U.S. Pat. No. 4,168,247 to Hayden et al, there is described a preparation procedure for catalysts identified by the numbers 34–37 which consists of a silver-first order of addition. The alkali metal promoters were dissolved in water with further addition of methanol, and the resulting solution used to impregnate the carrier.

Japanese Patent Application No. 142,421/78 (Kokai No. 79,193/79) discloses a "post-treatment" of a used or stabilized silver catalyst by impregnating such catalyst with a solution containing an alkali metal promoter, an organic compound capable of forming a complex salt with silver ion and an alcohol of 1 to 4 carbon atoms. No alcohol other than methanol was used in the impregnating solution described in the examples. A further distinction between the process of the reference and the present invention resides in the fact that the improved efficiencies achieved in the examples of the reference can be attributable to the presence of an oxide of nitrogen in the catalyst (see, for example, GB No. 2,014,133A which discloses the beneficial effects of nitrates or nitrite forming substances in the manufacture of ethylene oxide), rather than, the promoting effect of alkali metal in accordance with the present invention.

SUMMARY OF THE INVENTION

The invention describes a process for preparing a supported silver catalyst for the production of ethylene oxide by the vapor phase oxidation of ethylene with an oxygen-containing gas, the catalyst produced by such process and the use of such silver catalyst for ethylene oxide manufacture. The process comprises impregnating a porous catalyst support with a solution comprising a solvent or a solubilizing agent, and silver salt in an amount sufficient to deposit the desired amount of silver on said support. The impregnated support is then treated to convert at least a fraction of the silver salt to silver metal and effect deposition of silver on the surface of said support. Following silver deposition, the support is impregnated with a liquid containing more than 30%, by volume, of an organic solvent capable of forming a complex with silver ion, and a compound of at least one metal cation promoter in an amount sufficient to deposit the desired amount of metal cation on said support. In accordance with another embodiment of the invention the impregnating solution containing the metal promoters is kept substantially free of lower alcohols, which as used herein refers to alcohols containing from 1 to 4 carbon atoms. The impregnated support is thereafter treated to effect deposition of the promoter on the surface of said support.

The catalyst preparation process of the invention, in its broadest aspect, concerns a process wherein silver and a metal promoter are sequentially deposited on the surfaces of a porous carrier by a silver-first method. The particular metal promoter employed is not critical to the invention and may include one or more alkali metals, such as lithium, sodium, potassium, rubidium and/or cesium; one or more alkaline earth metals, such as, barium, magnesium and strontium; or one or more of the other known promoters, such as thallium, gold, tin, antimony and rare earths; and the like. For purposes of convenience, the catalyst preparation process of the invention is described below in terms of a silver-first method of preparation wherein the promoter is selected from among alkali metals, it being recognized that other promoters of silver catalysts, such as those mentioned above, may optionally be substituted for or added to alkali metals in such process.

The process of the invention is predicated on the discovery that a catalyst preparation procedure employing a silver-first addition of silver and metal cation to a porous carrier can provide catalysts as efficient as those produced by the coincidental deposition of the same onto the same or similar carrier provided that the solvent for the metal cation impregnating solution is selected in accordance with the invention. That is, contrary to prior art experiences with silver-first methods of preparation wherein the resulting catalysts invariably are less efficient, even at their optimum, than corresponding catalysts prepared by a method of coincidental deposition, the catalysts of the invention provide improved selectivities to ethylene oxide and are equally as efficient as catalysts produced by coincidental methods of preparation.

As used herein with reference to the silver catalyst and process of the invention, the term "optimum" efficiency is defined as the highest efficiency obtainable at any concentration of promoter for a given silver content, catalyst carrier, and method of preparation when tested at fixed operating conditions.

The solvent employed in the metal cation impregnating solution is an essential feature of the present invention. The organic solvents useful for the invention are characterized by their capability of forming a silver complex in the presence of silver ion. Contrary to the disclosure in the aforementioned Japanese Patent Application No. 142,421/78, it has been found that such silver complex forming solvents can be effectively used in a silver-first sequential process of preparation in amounts in excess of 30%, by volume, of the impregnating solution. Indeed, as hereinafter described, depending upon the solubility of the metal promoter in such solvents, they are advantageously employed in the impregnating solution in concentrations as high as possible, generally above 50 weight %, and preferably about 80% or higher by weight of solution. Further, unlike the process of the aforementioned Japanese Application, the presence of a lower alcohol in the impregnating solution is not required in the method of the present invention. The term "lower alcohol" as used in this specification and the claims means an alcohol of not more than four carbon atoms.

Suitable solvents used for impregnating the metal promoter in accordance with the invention include, among others, amino alcohols such as monoethanolamine; alkylene diamines such as ethylenediamine; alkyl amines such as isopropylamine; amino ethers such as bis(2-amino) ethyl ether; and amides such as formamide.

In addition to the aforementioned improved catalyst efficiencies, another important characteristic of the process of the invention and one which provides an unexpected advantage over conventional methods of catalyst preparation relates to the fact that the amount of alkali metal promoter deposited upon the carrier need not be as narrowly controlled as in the prior art to achieve an optimum catalyst efficiency. It is known in the art that the coincidental method of producing ethylene oxide catalysts requires strict control of the amount of promoter added to the carrier in order to maximize the catalyst efficiency for the given carrier and silver content. The effect of promoter concentration on catalyst efficiency is graphically demonstrated by the drawing presented in the above-mentioned U.S. Ser. No. 216,188 (the parent application of the Nielsen et al U.S. patent ) which depicts the relative effects of cesium, rubidium and potassium as respective promoters in enhancing the efficiency of a silver catalyst to make ethylene oxide. Curves A, B and C of the drawing show the appropriate concentration ranges in which potassium, rubidium and cesium, respectively, provide the greatest degree of selectivity enhancement. From the curves it is evident that the amount of alkali metal which must be added to the carrier is critical if the maximum catalyst efficiency is to be realized. By way of comparison, in the present process the promoter concentration required to produce catalysts having optimum selectivities to ethylene oxide is not as narrowly critical. For example, the range of alkali metal concentrations capable of providing the optimum efficiency is far broader than the corresponding range for catalysts produced by coincidental methods of preparation in which alkali metals are the promoters. Thus, an important advantage of the present process resides in the fact that commercial-scale batches of ethylene oxide catalysts can be manufactured within a relatively broad specification of the metal content and still achieve optimum efficiency.

When alkali metals are the promoters, the amount of alkali metal needed on the catalyst support according to the process of this invention to achieve an optimum efficiency is typically at least 10% greater than that amount of like alkali metal which provides the maximum enhancement of efficiency when used in a coincidental method of preparation with the same amount of silver and the same catalyst support. Even though this is the case, the amount of alkali metal to achieve optimum efficiency is still not as narrowly critical and will vary depending upon silver content, the catalyst support employed, the solvent for the alkali metal impregnating solution, and other catalyst preparation variables.

CATALYST PREPARATION

The catalyst preparation method of the invention concerns a silver-first sequential addition of silver and metal cation promoter to a porous carrier. Stated simply, the process involves a sequence of steps carried out in the following order:

First, impregnating a porous catalyst support by immersing same in a silver-containing impregnating solution;

Second, treating the impregnated support to effect deposition of silver on the surface of said support;

Third, impregnating the product of step two by immersing same in a metal cation-containing impregnating solution as defined herein; and Fourth, treating the impregnated support to effect deposition of the metal promoter on the surface of said support.

Silver deposition is generally accomplished by heating the impregnated carrier at elevated temperatures to evaporate the liquid within the support and effect deposition of the silver onto the interior and exterior carrier surfaces. Alternatively, a coating of silver may be formed on the carrier from an emulsion or slurry containing the same followed by heating the carrier as described above. Impregnation of the carrier is generally the preferred technique for silver deposition because it utilizes silver more efficiently than coating procedures, the latter being generally unable to effect substantial silver deposition onto the interior surfaces of the carrier.

The silver solution used to impregnate the carrier is comprised of a silver salt or compound in a solvent or complexing/solubilizing agent such as the silver solutions disclosed in the art. The particular silver salt employed is not critical and may be chosen, for example, from among silver nitrate, silver oxide or silver carboxylates, such as, silver acetate, oxalate, citrate, phthalate, lactate, propionate, butyrate and higher fatty acid salts.

A wide variety of solvents or complexing/solubilizing agents may be employed to solubilize silver to the desired concentration in the impregnating medium. Generally, the silver concentration in the impregnating medium should be sufficient to deposit on the support from about 2 to about 20 wt. % of silver based on the total weight of the catalyst. Among solvents disclosed in the art as being suitable for this purpose are lactic acid (U.S. Pat. Nos. 2,477,435 to Aries; and 3,501,417 to DeMaio); ammonia (U.S. Pat. No. 2,463,228 to West et al); alcohols, such as ethylene glycol (U.S. Pat. Nos. 2,825,701 to Endler et al; and 3,563,914 to Wattimena); and amines and aqueous mixtures of amines (U.S. Pat. Nos. 2,459,896 to Schwartz; 3,563,914 to Wattimena, 3,702,259 to Nielsen; and 4,097,414 to Cavitt).

Following impregnation of the catalyst carrier with silver, the impregnated carrier particles are separated from any remaining non-absorbed solution or slurry. This is conveniently accomplished by draining the excess impregnating medium or alternatively by using separation techniques, such as, filtration or centrifugation. The impregnated carrier is then generally heat treated (e.g., roasted) to effect decomposition and reduction of the silver metal salt to metallic silver. Such roasting may be carried out at a temperature of from about 100° C. to 900° C., preferably from 200° C. to 700° C., for a period of time sufficient to convert substantially all of the silver salt to silver metal. In general, the higher the temperature, the shorter the required reduction period. For example, at a temperature of from about 400° C. to 900° C., reduction may be accomplished in about 1 to 5 minutes. Although a wide range of heating periods have been suggested in the art to thermally treat the impregnated support, (e.g., U.S. Pat. No. 3,563,914 suggests heating for less than 300 seconds to dry but not roast reduce the catalyst; U.S. Pat. No. 3,702,259 discloses heating from 2 to 8 hours at a temperature of from 100° C. to 375° C. to reduce the silver salt in the catalyst; and U.S. Pat. No. 3,962,136 suggests ½ to 8 hours for the same temperature range) it is only important that the reduction time be correlated with temperature such that substantially complete reduction of the silver salt to metal is accomplished. A continuous or step-wise heating program may be used for this purpose.

Impregnation of the carrier with a solution containing a promoter salt or compound is carried out after silver deposition has been effected. The impregnating solution is prepared using one or more solvents as herein defined and contains an amount of promoter sufficient to achieve the desired concentration of promoter in the finished catalyst. The impregnated carrier particles are conveniently separated from any remaining non-absorbed solution by draining the excess impregnating solution or alternatively by using separation techniques, such as, filtration and centrifugation. The impregnated carrier is then generally heat treated at ambient or sub-atmospheric pressure to remove the solvent (or solvents) present and deposit (with or without decomposition) the alkali metal ions on to the silver and carrier surfaces. Such heating may be carried out at a temperature of from about 50° C. to 900° C., preferably from about 100° C. to 700° C. and most preferably from about 200° C. to about 600° C.

Suitable alkali metal promoter compounds include all those soluble in the particular solvent or solubilizing agent employed. Accordingly, inorganic and organic compounds of alkali metals, such as, nitrates, halides, hydroxides, sulfates and carboxylates may be used. An inherent advantage of the process of the invention is that it allows the use of certain promoter compounds which could not ordinarily be used in conjunction with known coincidental methods of preparation because of the incompatibility of such salts with the impregnating solution used in the latter processes. As an illustration, alkaline earth salts such as salts of barium, calcium and magnesium can readily be solubilized in an impregnating solution and deposited upon the carrier in accordance with the process of the invention, but can not be added to an impregnating solution containing, for example, oxalic acid or carboxylic acid, solutions commonly employed in conventional coincidental methods of preparation for purposes of silver solubilization.

The types of solvents useful for preparing the promoter impregnating solution are set forth above. Such solvents may be employed individually or in various combinations with each other provided that the salt of the desired promoter is sufficiently soluble therein. In the event that the promoter salt is not sufficiently soluble in the organic solvent to provide the desired concentration in the resulting impregnating solution, water may be added as a co-solvent for the promoter salt. Generally, organic solvent concentrations of 50 wt. % and higher are commonly employed for impregnation. In general, it is preferred that the concentration of organic solvent in the impregnating solution be as high as possible.

Heat treatment of the impregnated carriers is preferably carried out in air, but a nitrogen, carbon dioxide or hydrogen atmosphere may also be employed. The equipment used for such heat treatment may use a static or flowing atmosphere of such gases to effect reduction.

The particle size of silver metal deposited upon the carrier is a function of the catalyst preparation procedure employed. Thus, the particular choice of solvent and/or complexing agent, silver salt, heat treatment conditions and catalyst carrier may affect, to varying degrees, the size of the resulting silver particles. For carriers of general interest for the production of ethylene oxide, a distribution of silver particle sizes in the range of 0.05 to 2.0 microns is typically obtained.

CARRIER SELECTION

The catalyst carrier employed in practicing the invention may be selected from conventional, porous, refractory materials which are essentially inert to ethylene, ethylene oxide and other reactants and products at reaction conditions. These materials are generally labelled as "macroporous" and consist of porous materials having surface areas less than 10 m$^2$/g (square meters per gram of carrier) and preferably less than 1 m$^2$/g. The surface area is measured by the conventional B.E.T. method described by Brunauer, S., Emmet, P., and Teller, E., in J. Am. Chem. Soc. Vol. 60, pp 309–316, (1928). They typically possess pore volumes in the range of about 0.15–0.8 cc/g. A more preferred range is about 0.2–0.6 cc/g. Pore volumes may be measured by conventional mercury porosimetry or water absorption techniques. Median pore diameters for the above-described carriers range from about 0.01 to 100 microns, a more preferred range being from about 0.5 to 50 microns.

Preferably, the carrier should not contain ions which are exchangeable with the metal cations supplied to the catalyst, either in the preparation or use of the catalyst. If the carrier contains such ion, the ion should be removed by standard chemical techniques such as leaching.

The chemical composition of the carrier is not narrowly critical. Carriers may contain fused or bonded particles of, for example, of alpha-alumina, silicon carbide, silicon dioxide, zirconias, magnesia and various clays. In general, alpha-alumina based materials are preferred. These alpha-alumina based materials may be of very high purity, i.e., 98+weight % alpha-alumina, the remaining components being silica, alkali metal oxides (e.g., sodium oxide) and trace amounts of other metal and non-metal impurities; or they may be of lower purity, i.e., about 80 weight % alpha-alumina, the balance being a mixture of silicon dioxide, various alkali oxides, alkaline earth oxides, iron oxide, and other metal and non-metal oxides. The lower purity carriers are formulated so as to be inert under catalyst preparation and reaction conditions. A wide variety of such carriers are commercially available. The carriers are preferably shaped, typically in the form of pellets, extruded particles, spheres, rings and the like, for use in commercial reactors. The size of the carriers may vary from about 1/16" to 1/1". The carrier size and shape is chosen to be consistent with the type of reactor employed. In general, for fixed bed reactor applications, sizes in the range of ⅛" to ⅜" have been found to be most suitable in the typical tubular reactor used in commercial operations.

ETHYLENE OXIDE PRODUCTION

The silver catalysts of the invention are particularly suitable for use in the production of ethylene oxide by the vapor phase oxidation of ethylene with molecular oxygen. The products of the reactions are ethylene oxide and CO$_2$ as a consequence of the following two competing reactions:

$$C_2H_4 + \tfrac{1}{2}O_2 \rightarrow C_2H_4O \qquad (1)$$

$$C_2H_4 + 3O_2 \rightarrow 2CO_2 + 2H_2O \qquad (2)$$

The success in making reaction (1) more favored results in higher process efficiencies to ethylene oxide. The reaction conditions for carrying out the oxidation reaction are wellknown and extensively described in the literature. This applies to reaction conditions, such as, temperature, pressure, residence time, concentration of reactants, diluents (e.g., nitrogen, methane and recycled CO$_2$), inhibitors (e.g., ethylene dichloride) and the like. In addition, the desirability of recycling unreacted feed, or employing a single-pass system, or using successive reactions to increase ethylene conversion by employing reactors in series arrangement can be readily determined by those skilled in the art. The particular mode of operation selected will usually be dictated by process economics.

Generally, the process is carried out by continuously introducing a feed stream containing ethylene and oxygen to a catalyst-containing reactor at a temperature of from about 200° to 300° C., and a pressure which may vary from one atmosphere to about 30 atmospheres depending upon the mass velocity and productivity desired. Residence times in large-scale reactors are generally on the order of about 1–5 seconds. Oxygen may be supplied to the reaction in an oxygen-containing stream, such as, air or as commercial oxygen. The resulting ethylene oxide is separated and recovered from the reaction products using conventional methods. By-product CO$_2$ is usually recycled in part with the unreacted ethylene to the reaction in commercial operations.

CATALYST TESTING

The catalysts cited in the Tables of the Examples below were all evaluated under standard test conditions using backmixed, bottom-agitated "magnedrive" autoclaves as described in FIG. 2 of the paper by J.M. Berty entitled "Reactor For Vapor Phase-Catalytic Studies", in Chemical Engineering Progress, Vol. 70, No. 5, pages 78–84, 1974. The reactor was operated at 1.0 mole % ethylene oxide in the outlet gas under the following standard inlet conditions:

| Component | Mole % |
| --- | --- |
| Oxygen | 6.0 |
| Ethylene | 8.0 |
| Ethane | 0.50 |
| Carbon Dioxide | 6.5 |
| Nitrogen | Balance of Gas |
| Parts per millon Ethylene Chloride | 7.5 |

The pressure was maintained constant at 275 psig and the total outlet flow maintained at 22.6 SCFH.[1] The outlet ethylene oxide concentration was maintained at 1.0% by adjusting the reaction temperature. Thus, temperature (°C.) and catalyst efficiency are obtained as the responses describing the catalyst performance.
(1) SCHF refers to cubic feet per hour at standard temperature and pressure, namely, 0° C. and one atmosphere.

A typical catalyst test procedure is comprised of the following steps:

1. 80 cc of catalyst is charged to a backmixed autoclave. The volume of catalyst is measured in a 1" I.D. graduated cylinder after tapping the cylinder several times to thoroughly pack the catalyst. The weight of the catalyst is noted.

2. The backmixed autoclave is heated to about reaction temperature in a nitrogen flow of 20 SCFH with the fan operating at 1500 rpm. The nitrogen flow is then discontinued and the above-described feed stream is introduced into the reactor. The total gas outlet flow is adjusted to 22.6 SCFH. The temperature is adjusted over the next few hours so that the ethylene oxide concentration in the outlet gas is approximately 1.0%.

3. The outlet oxide concentration is monitored over the next 4–6 days to make certain that the catalyst has reached its peak steady state performance. The temperature is periodically adjusted to achieve 1% outlet oxide. The selectivity of the catalyst to ethylene oxide and the temperature are thus obtained.

The standard deviation of a single test result reporting catalyst efficiency in accordance with the procedure described above is 0.7% efficiency units.

It should be noted that the above-described back mixed autoclave generates lower efficiencies than tubular reactors, hence, the efficiencies described herein are not directly comparable with those obtained in a tubular reactor. In addition, the catalyst particles tested in the following examples are shaped for use in commercial sized tubular reactors. Such particles are known to yield lower efficiencies than crushed catalyst or catalyst made on a crushed support, but they have a significant advantage for operation in a commercial reactor in that they do not create an undesirable pressure drop across the catalyst bed as would crushed catalyst or catalyst made on a crushed support.

EXAMPLE 1

A catalyst containing 13 weight % Ag was prepared as hereinafter described on an alpha-alumina carrier "A" shaped as a ring having a diameter of 5/16", a length of 5/16" and ⅛" diameter hole. The carrier had the following chemical composition and physical properties.

| Chemical Composition of Carrier "A" | |
|---|---|
| Alpha-Alumina | 98.6 wt. % |
| Silicon Dioxide | 0.74 wt. % |
| Calcium Oxide | 0.22 wt. % |
| Sodium Oxide | 0.16 wt. % |
| Ferric Oxide | 0.14 wt. % |
| Potassium Oxide | 0.03 wt. % |
| Magnesium Oxide | 0.03 wt. % |

| Physical Properties of Carrier "A" | |
|---|---|
| Surface Area[1] | 0.3 m²/g |
| Pore Volume[2] (or water absorption) | 0.50 cc/g |
| Packing Density[3] | 0.70 g/ml |
| Median Pore Diameter | 21 microns |

| Pore Size Distribution, % Total Pore Volume (% TPV)[4] | |
|---|---|
| Pore Size, Microns | % TPV |
| 0.1–1.0 | 1.5 |
| 1.0–10.0 | 38.5 |
| 10.0–30.0 | 20.0 |
| 30–100 | 32.0 |
| >100 | 8.0 |

[1]Method of measurement described in "Adsorption, Surface Area and Porosity", S. J. Gregg and K. S. W. Sing, Academic Press (1967), pages 316–321.
[2]Method of Measurement as described in ASTM C20-46
[3]Calculated value based on conventional measurement of the weight of the carrier in a known volume container.
[4]Method of measurement described in "Application of Mercury Penetration to Materials Analysis", C. Orr Jr., Powder Technology, Vol. 3, pp. 177–123 (1970).

The carrier "A" was impregnated under vacuum as hereinafter described with a solution of silver salts which was prepared at a concentration such that the finished catalyst contained the desired amount of silver. The required concentration of silver in solution for the given carrier is calculated from the packing density (grams/cc) and the pore volume of the carrier which are either known or readily determined. Assuming that all of the silver in the impregnating solution contained in the pores of carrier "A" is deposited upon the carrier, approximately 23.6 weight % silver in solution is needed to prepare a catalyst containing about 13 weight % silver.

Preparation Of Silver Impregnating Solution 774.9 gms of ethylenediamine (high purity grade) was mixed with 1600 g of distilled water with continuous stirring in a 7 liter stainless steel beaker containing a three inch stirring bar, the vessel being mounted on a 6"×6" magnetic stirrer-hot plate. The ingredients were added to the vessel in the order described with constant stirring. The resulting solution was cooled to 25° C. and 812 g of oxalic acid dihydrate (reagent grade) was added in small portions, with continuous stirring, at a rate which maintained the temperature below 50° C. Silver oxide powder, 1423.5 g, (Handy and Harmon, 850 Third Avenue, New York, N.Y. 10022) was then added intermittently to the aqueous ethylenediamine oxalic acid solution while maintaining the temperature of the solution below 50° C. Finally, 283 g of monoethanolamine and 703 g of distilled water were added to bring the total volume of the impregnating solution to 4000 cc. The specific gravity of the resulting solution was about 1.385.

Catalyst Preparation

A 2636 grams charge of carrier "A" was placed in a 5 liter, round bottomed vessel equipped with a side arm fitted with a stopcock connected to a three foot long, ¼" O.D. tubing for the introducion of the impregnating solution which was contained in the above-described 7 liter stainless steel beaker located adjacent to the vessel. The vessel containing the carrier was evacuated to approximately 2 inches of mercury pressure for about 20 minutes after which the impregnating solution was slowly added to the carrier by opening the stopcock between the vessel and the beaker containing the impregnating solution until the carrier was completely immersed in solution. The vessel was then opened to the atmosphere to achieve atmospheric pressure, the carrier remaining immersed in the impregnating solution at ambient conditions for about one hour and thereafter drained of excess solution for about 30 minutes.

The impregnating carrier was removed from the vessel and heat treated as follows to effect reduction of the silver salt. The impregnated carrier was spread out in a single layer of pellets on a 2⅜" wide endless stainless steel belt (spiral weave) and transported through a 2"×2" square heating zone for 2.5 minutes, the heating zone being maintained at 500° C. by passing hot air upward through the belt and about the catalyst particles at the rate of 266 SCFH. The hot air was generated by passing it through a 5 ft. long ×2" I.D. stainless steel pipe which was externally heated by an electric furnace (Lindberg TM tubular furnace: 2½" I.D., 3 feet long heating zone) capable of delivering 5400 watts. The heated air in the pipe was discharged from a square 2"×2" discharge port located immediately beneath the moving belt carrying the catalyst carrier. After being roasted in the heating zone, the silver impregnated catalyst was weighed, and based upon the weight gain of the carrier, was calculated to contain 13.1 weight % silver. The silver-containing catalyst is referred to as catalyst 1.

Addition of Promoters

To demonstrate the effect which the solvent in the alkali metal impregnating solution has on the efficiency of the finished catalyst, five (5) catalysts of similar composition were prepared (1A-1E) using a different impregnating solution for each one, each solution containing a different solvent as described below. Catalysts containing 13.1 wt. % silver, 0.00906 wt. % cesium and 0.00268 wt. % potassium were prepared from the above described catalyst 1 by the sequential addition of cesium and potassium promoters in accordance with the following general procedure.

Each of the impregnating solutions used to prepare catalysts 1A through 1E was prepared by adding (a) 5.825 ml of an aqueous cesium hydroxide solution containing 0.0566 g of cesium and (b) 4.456 ml of an aqueous potassium carbonate solution containing 0.0167 g of potassium, to a 250 ml graduated cylinder. To each of the graduated cylinders there was added one of solvents A through E, identified below, in an amount sufficient to provide 250 ml of total solution.

SOLVENTS

A. Water
B. A solution of 80 wt. % water, 20 wt. % monoethanolamine.
C. A solution of 50 wt. % water, 50 wt. % monoethanolamine.
D. Monoethanolamine.
E. A solution of water-ethylenediamine-oxalic acid-monoethanolamine as described above in the preparation of catalyst 1, but containing no silver.

For the preparation of each catalyst, a 100 g sample of catalyst 1 was placed in a 12" long×1.5" I.D. glass cylindrical vessel equipped with a side arm fitted with a stopcock so as to allow the evacuation of the vessel using a vacuum pump. A 500 ml separatory funnel containing one of the impregnating solutions described above was inserted through a rubber stopper in the top of the vessel. The impregnating vessel containing catalyst 1 was evacuated to approximately 2 inches of mercury pressure for about 20 minutes after which the impregnating solution was slowly added to the carrier by slowly opening the stopcock between the separatory funnel and the impregnating vessel until catalyst 1 was completely immersed. Following the addition of solution, the system was opened to the atmosphere, catalyst 1 remaining immersed in the impregnating solution at ambient conditions for about 30 minutes. The impregnated carrier was drained of excess solution and heat treated to effect deposition of alkali metal on the carrier in the same manner as described above with regard to the preparation of catalyst 1. The finished catalysts prepared from the impregnating solutions containing one of the solvents A-E are designated 1A, 1B, 1C, 1D and 1E, respectively.

Table I below summarizes the test results for catalysts 1A through 1E when used for the oxidation of ethylene in accordance with the procedure detailed above.

TABLE I

| Catalyst | Selectivity, % | Temperature °C. |
|----------|----------------|-----------------|
| 1A | 70.6 | 261.4 |
| 1B | 71.8 | 257.5 |
| 1C | 73.7 | 252.4 |
| 1D | 74.0 | 256.8 |
| 1E | 75.3 | 251.9 |

As noted from Table I, catalyst 1A, which was prepared in accordance with the method of the prior art, provided the lowest selectivity in comparison with catalysts 1B-1E, prepared by the method of the invention.

What is claimed is:

1. In the process for preparing a supported silver catalyst for the production of ethylene oxide by the vapor phase oxidation of ethylene with an oxygen-containing gas comprising:
   (a) impregnating a porous catalyst support with a solution comprising a solvent or a solublizing agent, and silver salt in an amount sufficient to deposit the desired amount of silver on said support;
   (b) treating the impregnated support to convert at least a fraction of the silver salt to silver metal and effect deposition of silver on the surface of said support;
   (c) impregnating the support treated in step (b) with a solution containing a solvent and a compound of at least one metal cation promoter in an amount sufficient to deposit the desired amount of promoter on said support; and
   (d) treating the impregnated support produced in step (c) to effect disposition of said promoter on the surface of said support,
   the improvement comprising using in step (c) a solution comprising at least 50 wt. % of an organic solvent capable of forming a complex with silver ion and selected from the group consisting of alkyl amines, alkylene diamines, amino alcohols, amino ethers and amides and at least one compound of an alkali metal promoter.

2. A process as in claim 1 wherein said organic solvent is an amino alcohol.

3. A process as in claim 1 wherein said organic solvent is an alkylenediamine.

4. A process as in claim 1 wherein the solution used in step (c) thereof is substantially free of a lower alcohol.

5. A process as in claim 1 wherein said promoter is an alkali metal selected from the group consisting of cesium, potassium, lithium, sodium, rubidium and mixtures thereof.

6. A process as in claim 5 wherein the amount of alkali metal deposited on the catalyst support is at least 10% greater than that amount of like alkali metal which provides the maximum enhancement of efficiency when used in a coincidental method of preparation with the same amount of silver and the same catalyst support.

7. A process as in claim 1 wherein said catalyst contains silver in an amount of from about 2% to about 20% based on the total weight of the catalyst.

8. A process for preparing a supported silver catalyst for the production of ethylene oxide by the vapor phase oxidation of ethylene with an oxygen-containing gas comprising:
(a) impregnating a porous catalyst support with a solution comprising a solvent or a solubilizing agent, and silver salt in an amount sufficient to deposit the desired amount of silver on said support;
(b) treating the impregnated support to convert at least a fraction of the silver salt to silver metal and effect deposition of silver on the surface of said support;
(c) impregnating the support treated in step (b) with a solution containing more than 30%, by volume, of at least one liquid organic solvent capable of forming a complex with silver ion and selected from the group consisting of amino alcohols, alkylene diamine, alkyl amines, amino ethers and amides, and a compound of at least one alkali metal promoter in an amount sufficient to deposit the desired amount of promoter on said support wherein said solution is substantially free from a lower alcohol; and
(d) treating the impregnated support produced in step (c) to effect deposition of said promoter on the surface of said support.

9. A process for preparing a supported silver catalyst for the production of ethylene oxide by the vapor phase oxidation of ethylene with an oxygen-containing gas comprising:
(a) impregnating a porous catalyst support with a solution comprising a solvent or a solubilizing agent, and silver salt in an amount sufficient to deposit the desired amount of silver on said support;
(b) treating the impregnated support to convert at least a fraction of the silver salt to silver metal and effect deposition of silver on the surface of said support;
(c) impregnating the support treated in step (b) with a solution containing at least about 50%, by volume, of an organic solvent selected from the group consisting of organic liquids capable of forming a complex with silver ion, and a compound of at least one alkali metal promoter in an amount sufficient to deposit the desired amount of promoter on said support; and
(d) treating the impregnated support produced in step (c) to effect deposition of said promoter on the surface of said support.

* * * * *